United States Patent
Ishihara et al.

(10) Patent No.: US 8,507,715 B2
(45) Date of Patent: Aug. 13, 2013

(54) METHOD FOR PRODUCING β-AMINOCARBONYL COMPOUND

(75) Inventors: Kazuaki Ishihara, Nagoya (JP); Manabu Hatano, Nagoya (JP); Takahiro Horibe, Nagoya (JP)

(73) Assignee: National University Corporation Nagoya University, Nagoya (JP)

( * ) Notice: Subject to any disclaimer, the term of this patent is extended or adjusted under 35 U.S.C. 154(b) by 0 days.

(21) Appl. No.: 13/700,746

(22) PCT Filed: Jun. 22, 2011

(86) PCT No.: PCT/JP2011/064220
§ 371 (c)(1),
(2), (4) Date: Nov. 29, 2012

(87) PCT Pub. No.: WO2012/002203
PCT Pub. Date: Jan. 5, 2012

(65) Prior Publication Data
US 2013/0079543 A1    Mar. 28, 2013

(30) Foreign Application Priority Data
Jul. 1, 2010   (JP) .................................. 2010-150999

(51) Int. Cl.
*C07C 231/12*   (2006.01)
*B01J 31/24*    (2006.01)

(52) U.S. Cl.
USPC ................... 560/38; 560/27; 560/44; 560/19; 560/8; 560/40

(58) Field of Classification Search
CPC .. C07C 231/12; C07C 271/06; C07C 271/28; C07C 269/06; C07C 227/08; C07C 229/30; C07C 227/18; C07C 2101/14; B01J 31/24; B01J 31/2409; C07D 215/56
USPC ............................. 560/38, 27, 44, 19, 8, 40
See application file for complete search history.

(56) References Cited

U.S. PATENT DOCUMENTS
2008/0228000 A1   9/2008 Deng

FOREIGN PATENT DOCUMENTS
JP    A-2008-163022   7/2008
JP    A-2010-207786   9/2010

OTHER PUBLICATIONS

Hatano et al. (Magnesium(II)-Binaphtholate as a Practical Chiral Catalyst for the Enantioselective Direct Mannich-Type Reaction with Malonates, Organic Letters, vol. 12, No. 15, pp. 3502-3505).*
Marigo et al., "Direct Catalytic Asymmetric Mannich Reactions of Malonates and β-Keto Esters," *Chem. Eur. J.*, vol. 9, pp. 2359-2367, 2003.
Tillman et al., "Direct enantio- and diastereoselective Mannich reactions of malonate and β-keto esters with N-Boc and N-Cbz aldimines catalysed by a bifunctional cinchonine derivative," *The Royal Society of Chemistry*, pp. 1191-1193, 2006.
Song et al., "The Mannich Reaction of Malonates with Simple Imines Catalyzed by Bifunctional Cinchona Alkaloids: Enantioselective Synthesis of β-Amino Acids," *J. Am. Chem. Soc.*, vol. 128, No. 18, pp. 6048-6049, 2006.
Chen et al., "A Bench-Stable Homodinuclear $Ni_2$-Schiff Base Complex for Catalytic Asymmetric Synthesis of α-Tetrasubstituted *anti*-α, β-Diamino Acid Surrogates," *J. Am. Chem. Soc.*, vol. 130, No. 7, pp. 2170-2171, 2008.
Poisson et al., "Asymmetric Mannich Reaction of Malonates with Imines Catalyzed by a Chiral Calcium Complex," *J. Org. Chem.*, vol. 75, pp. 963-965, 2010.
Lee et al., "Organocatalytic Highly Enantioselective Mannich-Type Reactions of Fluoromalonate with N-Boc-Aldimines," *Special Topic*, Department of Chemistry, Soonchunhyang University, No. 11, pp. 1860-1864, 2010.
Du et al., "BINOLate-Magnesium Catalysts for Enantioselective Hetero-Diels-Alder Reaction of Danishefsky's Diene with Aldehydes," *European Journal of Organic Chemistry*, pp. 2248-2254, 2008.
Bolm et al., "Enantioselective Baeyer-Villiger Oxidations Catalyzed by Chiral Magnesium conplexes," *Synlett*, No. 9, pp. 1461-1463, 2001.
Kobayashi et al., "Chiral Zirconium Complex as Bronsted Base Catalyst in Asymmetric Direct-type Mannich Reactions," *Chemistry an Asian Journal*, vol. 5, pp. 493-495, 2010.
Aug. 16, 2011 International Search Report issued in International Patent Application No. PCT/JP2011/064220.
Feb. 12, 2013 International Preliminary Report on Patentability issued in International Patent Application No. PCT/JP2011/064220 (with translation).

* cited by examiner

*Primary Examiner* — Johann R Richter
*Assistant Examiner* — Blaine Doletski
(74) *Attorney, Agent, or Firm* — Oliff & Berridge, PLC

(57) ABSTRACT

An optically active β-aminocarbonyl compound is obtained by a Mannich reaction between an aldimine in which: nitrogen is protected and a malonic acid diester, in the presence of optically active BINOL and dialkyl magnesium (in which two alkyl groups are the same or different) in an amount 1 to 2 molar times the amount of the BINOL.

5 Claims, No Drawings

METHOD FOR PRODUCING β-AMINOCARBONYL COMPOUND

TECHNICAL FIELD

The present invention relates to a method for producing a β-aminocarbonyl compound.

BACKGROUND ART

Mannich reactions in which a carbonyl compound is added directly to an aldimine are one. Of the most important carbon-carbon bond formation reactions in organic synthesis because the product is an optically active β-aminocarbonyl compound. Among such Mannich reactions, there are known only several examples of a reaction in which a malonic acid diester is added to an aldimine (Non-Patent Literatures 1 to 6). Despite being an important reaction, development thereof has been considered to be difficult. On the other hand, as a reaction in which a magnesium complex of BINOL (1,1'-bi-2-naphthol) is used as a catalyst, hetero-Diels-Alder reactions and Baeyer-Villiger oxidation are known (Non-Patent Literatures 7 and 8).

CITATION LIST

Non-Patent Literature

Non-Patent Document 1: Chem. Eur. J. 2003, vol. 9, p 2359
Non-Patent Document 2: Chem. Commun., 2006, p 1191
Non-Patent Document 3: J. Am. Chem. Soc., 2006, vol. 128, p 6048
Non-Patent Document 4: J. Am. Chem. Soc., 2008, vol. 130, p 2170
Non-Patent Document 5: J. Org. Chem., 2010, vol. 75, 963
Non-Patent Document 6: Synthesis, 2010, p 1860
Non-Patent Document 7: Eur. J. Org. Chem., 2008, p 2248
Non-Patent Document 8: Synlett., 2001, p 1461

Disclosure of Invention

Although Mannich reactions in which a malonic acid diester is added to an aldimine using a catalyst have been reported in Non-Patent Literatures 1 to 6 described above, there are problems, such as a long reaction time, a low enantiomeric excess, and the need to use a catalyst having a complex structure. On the other hand, although reactions in which a magnesium complex of BINOL is used as a catalyst have been reported in Non-Patent Literatures 7 and 8, no attempts have been reported of the use thereof as a catalyst in a Mannich reaction.

The present invention has been achieved in order to solve the problems described above. It is a main object of the present invention to obtain a β-aminocarbonyl compound in high yield and with a high enantiomeric excess by carrying out a Mannich reaction between an aldimine and a malonic acid diester using a catalyst having a simple structure.

The present inventors have already reported, as a catalyst in a Mannich reaction in which a carbonyl compound Is added directly to an aldimine, a chiral lithium binaphtholate catalyst. However, this catalyst is not applicable in the case where the carbonyl compound is a malonic acid diester. Accordingly, studies have been conducted on a chiral magnesium binaphtholate catalyst. As a result, it has been found that the chiral magnesium binaphtholate catalyst is highly active in this reaction, and a product can be obtained in high yield and with a high enantiomeric excess, thus completing the present invention.

A method for producing a β-aminocarbonyl compound of the present invention comprises carrying out a Mannich reaction between an aldimine in which nitrogen is protected and a malonic acid diester, in the presence of optically active BINOL and dialkyl magnesium (in which two alkyl groups are the same or different) in an amount 1 to 2 molar times the amount of the BINOL, to obtain an optically active β-aminocarbonyl compound.

In the method for producing a β-aminocarbonyl compound according to the present invention, an optically active β-aminocarbonyl compound can be obtained in high yield and with a high enantiomeric excess. In this production method, it is believed that a magnesium binaphtholate complex corresponding to the optically active BINOL is generated in the system and serves as a catalyst, and an asymmetric Mannich reaction proceeds. This catalyst has a simple structure in which magnesium coordinates to BINOL, and can be easily prepared in the system, for example, using a commercially available reagent. The assumed reaction mechanism is exemplified below. Here, the reaction between tert-butylbenzylidene carbamate and dimethyl malonate is illustrated. It is assumed that the asymmetric Mannich reaction proceeds, for example, via the form of Bronsted acid-Bronsted base (shown on the left side), Lewis acid-Bronsted base (shown on the right side), or the like.

[Formula 1]

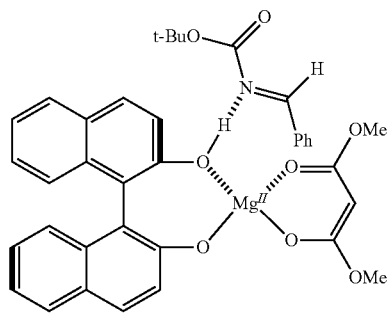

Bronsted acid-Bronsted base

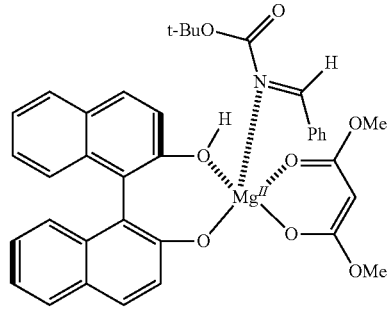

Lewis acid-Bronsted base

BEST MODES FOR CARRYING OUT THE INVENTION

A method for producing a β-aminocarbonyl compound of the present invention comprises carrying out a Mannich reaction between an aldimine in which nitrogen is protected and a malonic acid diester, in the presence of optically active BINOL and dialkyl magnesium (in which two alkyl groups are the same or different) in an amount 1 to 2 molar times the amount of the BINOL, to obtain an optically active β-aminocarbonyl compound.

The optically active BINOL, i.e., 1,1'-bi-2-naphthol, used in the method for producing β-aminocarbonyl compound according to the present invention exists in the R-form and the S-form because of asymmetric axes (chiral axes), but either can be used. It is believed that the BINOL reacts with a source of magnesium to form a magnesium binaphtholate complex, and this complex serves as a catalyst for the asymmetric Mannich reaction. Consequently, the amount of BINOL to be used is closely related to the amount of the catalyst to be used. The BINOL is used preferably in an amount of 1 mole percent to 20 mole percent, more preferably in an amount of 2.5 mole percent to 10 mole percent, relative to the reaction substrate. (e.g., the aldimine), although not particularly limited thereto. However, in some cases, depending on the structure of the reaction substrate and the structure of the catalyst, good results may be obtained even if the amount deviates from the range described above.

In the method for producing a β-aminocarbonyl compound according to the present invention, dialkyl magnesium is used in an amount 1 to 2 molar times the amount of BINOL. Usually, good results can be obtained by using dialkyl magnesium in an amount 1 molar times the amount of BINOL. However, for example, in the case where the reaction substrate has a heteroatom (group), such as an alkoxy group, dialkyl magnesium is used preferably in an amount more than 1 molar times, for example, 1.2 to 2.0 molar times or 1.5 to 2.0 molar times. Specifically, dialkyl magnesium is used preferably in an amount 1.5 molar times or 2 molar times. The reason for this is believed to be that magnesium coordinates to the oxygen atom of the alkoxy group in the reaction substrate, and the amount of magnesium constituting the catalyst decreases. Two alkyl groups in the dialkyl magnesium may be the same or different. The dialkyl magnesium is not particularly limited, and examples thereof include $Me_2Mg$, $Et_2Mg$, $n-Pr_2Mg$, $i-Pr_2Mg$, $n-Bu_2Mg$, $i-Bu_2Mg$, $sec-Bu_2Mg$, and $tert-Bu_2Mg$. Among these, in view of easy availability, $n-Bu_2Mg$ is preferable.

In the method for producing a β-aminocarbonyl compound according to the present invention, the aldimine used in the Mannich reaction is preferably a compound represented by $R^1$—CH=$NR^2$ (wherein $R^1$ is an aryl group or an ester group, and $R^2$ is tert-butoxycarbonyl (Boc), benzyloxycarbonyl (Cbz), or 2,2,2-trichloroethoxycarbonyl (Troc)). Examples of the aryl group include aromatic hydrocarbon groups, such as a phenyl group, a naphthyl group, a phenanthryl group, and an anthranil group; and aromatic heterocyclic groups, such as a furyl group, a thienyl group, and a pyridyl group. Furthermore, these compounds may have a substituent. In such a case, examples of the substituent include an alkyl group, an alkenyl group, a cycloalkyl group, an aryl group, an alkoxy group, and a halogen. Examples of the alkyl group include a methyl group, an ethyl group, an n-propyl group, an isopropyl group, an n-butyl group, an isobutyl group, a sec-butyl group, and a tert-butyl group. Examples of the alkenyl group include a vinyl group, an allyl group, a butenyl group, and a styryl group. Examples of the cycloalkyl group include a cyclopropyl group, a cyclopentyl group, and a cyclohexyl group. Examples of the aryl group include a phenyl group, a biphenyl group, a naphthyl group, and a binaphthyl group. Examples of the alkoxy group include a methoxy group, an ethoxy group, an n-propoxy group, an isopropoxy group, an n-butoxy group, an isobutoxy group, a sec-butoxy group, and a tert-butoxy group. Examples of the halogen include a fluorine atom, a chlorine atom, a bromine atom, and an iodine atom. Among these, the chlorine atom or the bromine atom is preferable. Furthermore, examples of the ester group include a methoxycarbonyl group, an ethoxycarbonyl group, an n-propylcarbonyl group, an isopropylcarbonyl group, an n-butoxycarbonyl group, an isobutoxycarbonyl group, a sec-butoxycarbonyl group, a tert-butoxycarbonyl group, and a phenoxycarbonyl group. $R^2$ is a protecting group. In the case where Boc is employed as the protecting group, deprotection can be performed under a strongly acidic condition, such as trifluoroacetic acid or a hydrochloric acid-ethyl acetate solution. In the case where Cbz is employed, deprotection can be performed by hydrogenation using palladium as a catalyst or Birch reduction. In the case where Troc is employed, deprotection can be performed by treatment with zinc powder-acetic acid or the like. Furthermore, $R^2$ is preferably any of the protecting groups described above, but may be an aryl group, such as a phenyl group, a 2-methoxyphenyl group, a 4-methoxyphenyl group, or a naphthyl group.

The malonic acid diester used in the method for producing a β-aminocarbonyl derivative according to the present invention is preferably a compound represented by $CHX(CO_2R^3)_2$ (wherein X is a hydrogen atom or a halogen atom, and $R^3$ is alkyl, allyl, benzyl, or aryl). Examples thereof include dimethyl malonate, diethyl malonate, di-n-propyl malonate, diisopropyl malonate, di-n-butyl malonate, diisobutyl malonate, di-sec-butyl malonate, di-tert-butyl malonate, diallyl malonate, dibenzyl malonate, diphenyl malonate, and the like, and also include compounds obtained by replacing one of two hydrogen atoms in the α positions of these diesters with a halogen atom. As the halogen atom, a chlorine atom or a bromine atom is preferable.

In the method for producing a β-aminocarbonyl derivative according to the present invention, the reaction solvent is not particularly limited, but preferably, an aromatic solvent, a halogenated hydrocarbon solvent, or an ether solvent is used. Examples of the aromatic solvent include toluene and xylene. Examples of the halogenated hydrocarbon solvent include methylene chloride, 1,1-dichloroethane, and 1,2-dichloroethane. Examples of the ether solvent include diethyl ether. Among these, toluene is preferable.

In the method for producing a β-aminocarbonyl derivative according to the present invention, the reaction temperature is not particularly limited, but is preferably −60° C. to 50° C., more preferably −40° C. to 30° C. (room temperature). Furthermore, the reaction time may be a period of time until the reaction substrate is consumed or the reaction stops, and is usually set in the range of several minutes to several hours. Furthermore, there is a possibility that the aldimine, which is a starting material in the Mannich reaction, may be decomposed by being mixed with moisture, and therefore, a dehydrating agent, such as magnesium sulfate or molecular sieves, may be added to the reaction system.

EXAMPLES

Example 1

Magnesium sulfate (100 mg) was added into a nitrogen-purged Schlenk reaction vessel, and drying was performed by heating with a heat gun for about 3 to 5 minutes under a reduced pressure (<5 Torr). The reaction vessel was cooled to room temperature while maintaining the reduced pressure, and nitrogen was introduced thereinto. Then, (R)-BINOL (7.1 mg, 0.025 mmol) and toluene (3 mL) were added into the reaction vessel, followed by through stirring. The mixture was cooled to −20° C., and n-Bu₂Mg (1.0 M heptane solution, 25.0 μL, 0.025 mmol) was added thereto, followed by stirring at −20° C. for 5 minutes. Subsequently, dimethyl malonate (62.9 μL, 0.55 mmol) was added thereto, and stirring was performed at −20° C. for 5 minutes. Lastly, as an aldimine, tert-butylbenzylidene carbamate (102.6 mg, 0.50 mmol) was added to the mixture, and stirring was performed at −20° C. for 3 hours. Completion of the reaction was confirmed by TLC, and the reaction was terminated by addition of a 1 M hydrogen chloride-methanol solution (2 mL). Ethyl acetate (10 mL) and water (5 mL) were added to the reaction mixture, and the resulting mixture was subjected to usual separation treatment. The aqueous layer was further extracted with ethyl acetate (10 mL×2 times). The extracted organic layer was washed with a saturated sodium chloride aqueous solution (10 mL) and dried over sodium sulfate, followed by filtration and concentration. The concentrate was subjected to silica gel column chromatography (hexane:ethyl acetate=5:1 to 2:1) for separation of a product. Thereby, a pure product was obtained in a yield higher than 99% (169 mg). Furthermore, the enantiomeric excess of the product was determined to be 92% ee (R) by high-performance liquid chromatography (hexane:isopropanol=9:1, 1.0 mL/min) with chiral column AD-H. In Example 1, (R)-BINOL and n-Bu₂Mg were each used in an amount of 5 mole percent relative to the aldimine.

It was possible to readily convert the resulting product into optically active β-lactam, which is useful as an intermediate for medical drugs and agricultural chemicals, as shown in the formula below, by converting the product into α-amino ester with hydrochloric acid treatment, followed by treatment with LDA.

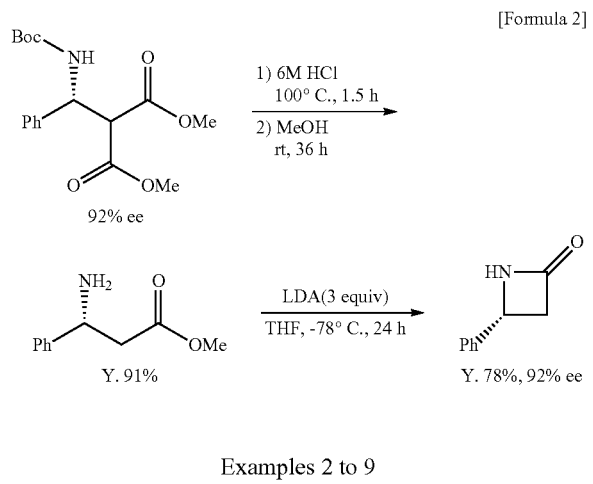

[Formula 2]

Examples 2 to 9

Asymmetric Mannich reactions between dimethyl malonate and various aldimines shown in Table 1 were carried out as in Example 1. The results thereof are shown in Table 1. In all of Examples 2 to 9, products were obtained with very high enantiomeric excesses. Note that the numerical values in brackets under the columns of yield and enantiomeric excess in Example 5 represent the results in the case where 5 mole percent of (R)-BINOL and 7.5 mole percent of n-Bu₂Mg were used. In Example 5, compared with the case where 5 mole percent of (R)-BINOL and 5 mole percent of n-Bu₂Mg were used, better results were obtained in the case where 5 mole percent of (R)-BINOL and 7.5 mole percent of n-Bu₂Mg were used. The reason for this is believed to be that, in the former, magnesium is chelated to the oxygen atom of the methoxy group of the aldimine, resulting in a reduction in the amount of catalyst species, while in the latter such a reduction in the amount of catalyst species can be prevented because the amount of n-Bu₂Mg is increased. This result shows that in some cases, depending on the structure of the aldimine, it is preferable to use n-Bu₂Mg in an amount larger than the amount of (R)-BINOL.

TABLE 1

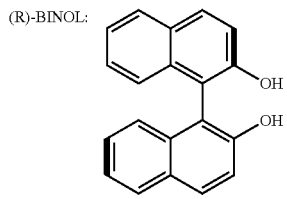 [SMILES: "(R)-BINOL:" ; Oc1ccc2ccccc2c1-c1c(O)ccc2ccccc12]

| | R¹ | R² | Yield (%) | ee (%) |
|---|---|---|---|---|
| Example 1 | Ph | Boc | >99 | 92 |
| Example 2 | Ph | Cbz | 98 | 82 |
| Example 3 | 4-ClC₆H₄ | Boc | 98 | 93 |
| Example 4 | 3-MeC₆H₄ | Boc | 94 | 87 |
| Example 5 | 3,4-(CH₃O)₂C₆H₃ | Boc | 55, [91] | 87, [90] |
| Example 6 | 2-Furyl | Boc | >99 | 90 |
| Example 7 | 3-Thienyl | Boc | >99 | 95 |
| Example 8 | 3-Pyridyl | Boc | 99 | 89 |
| Example 9 | 1-Naphthyl | Boc | 98 | 88 |

The spectrum data of the products obtained in Examples 1 to 9 are shown below.

Resulting product obtained in Example 1

¹H NMR (400 MHz, CDCl₃) δ 1.42 (s, 9H), 3.64 (s, 3H), 3.75 (s, 3H), 3.93 (brs,1H), 5.49 (brs, 1H), 6.16 (brs, 1H), 7.23-7.34 (m, 5H). ¹³C NMR (100 MHz, CDCl₃) δ 28.2 (3C), 52.5, 52.8, 53.3, 56.6, 79.7, 126.1 (2C), 127.6, 128.6 (2C), 139.3, 155.1, 167.5, 168.3. M.p. 95-97° C. IR. (KBr) 3375, 2982, 2954, 1737, 1689, 1521, 1294, 1245, 1173, 1011, 705 cm⁻¹. [α]_D²⁷=−14.8 (c 1.0, CHCl₃, 92% ee(R)) HRMS (FAB+) calcd for C₁₇H₂₃NNaO₆ [M+Na]⁺ 360.1423, found 360.1419. HPLC analysis; AD-H, n-hexane/i-PrOH=9/1, 1.0 mL/min, t_R=21.4 min (minor, S), 29.0 min (major, R).

Resulting product obtained in Example 2

¹H NMR (400 MHz, CDCl₃) δ 3.61 (s, 3H), 3.68 (s, 3H), 3.93 (brs, 1H), 5.07 (d, J=12.0 Hz, 1H), 5.11 (d, J=12.0 Hz, 1H), 5.55 (brs, 1H), 6.45 (brs, 1H), 7.10-7.55 (m, 10H). ¹³C NMR (100 MHz, CDCl₃) δ 52.7, 53.0, 54.0, 56.6, 67.0, 126.3 (2C), 127.9, 128.1 (2C), 128.1 (2C), 128.5 (2C), 128.8, 128.8 (2C), 136.4, 139.1, 155.8, 167.4, 168.4. IR (neat) 3335, 4954, 1736, 1507, 1240, 1152, 1044 cm⁻¹. [α]_D²⁴=+9.6 (c 1.0, CHCl₃, 82% ee (R)) HRMS (FAB+) calcd for C₂₀H₂₁NNaO₆

[M+Na]+ 394.1267, found 394.1261. HPLC analysis; AD-H, n-hexane/i-PrOH=9/1, 1.0 mL/min, $t_R$=46.8 min (minor, S), 67.0 min (major, R).

Resulting product obtained in Example 3

$^1$H NMR (400 MHz, CDCl$_3$) δ 1.41 (s, 9H), 3.65 (s, 3H), 3.75 (s, 3H), 3.88 (brs, 1H), 5.44 (brs, 1H), 6.16. (brs, 1H), 7.24 (d, J=8.4 Hz, 2H), 7.29 (d, J=8.4 Hz, 2H). $^{13}$C NMR (100 MHz, CDCl3) δ 28.2 (3C), 52.6, 52.7, 53.1, 56.5, 80.1, 127.7 (2C), 128.8 (2C), 133.6, 138.1, 155.1, 167.4, 168.3. IR (neat) 3421, 2978, 1717, 1491, 1244, 1161 cm$^{-1}$. $[α]_D^{23}$=−10.0 (c 1.00, CHCl$_3$, 93% ee (R)) HRMS (FAB+) calcd for C$_{17}$H$_{22}$ClNNaO$_6$ [M+Na]+ 394.1033, found 394.1042. HPLC analysis; AD-H, n-hexane/i-PrOH=9/1, 1.0 mL/min, $t_R$=28.5 min (major, R), 35.6 min(minor, S).

Resulting product obtained in Example 4

$^1$H NMR (400 MHz, CDCl$_3$) δ 1.42 (s, 9H), 2.33 (s, 3H), 3.64 (s, 3H), 3.74 (s, 3H), 3.91 (brs, 1H), 5.45 (brs, 1H), 6.14 (brs, 1H), 7.02-7.13 (m, 3H), 7.20 (t, J=7.2 Hz, 1H). $^{13}$C NMR (100 MHz, CDCl$_3$) δ 21.6, 28.4 (3C), 52.6, 53.0, 53.4, 56.8, 79.8, 123.2, 127.0, 128.5, 128.6, 138.3, 139.4, 155.2, 167.7, 158.5. IR (neat) 3428, 2977, 1718, 1497, 1366, 1243, 1164, 1046 cm$^{-1}$. $[α]_D^{24}$=−14.0 (c 1.00, CHCl$_3$, 87% ee (R)). HRMS (FAB+) calcd for C$_{18}$H$_{25}$NNaO$_6$ [M+Na]+ 374.1580, found 374.1574. HPLC analysis; AD-H, n-hexane/i-PrOH=9/1, 1.0 mL/min, $t_R$=17.9 min(minor, S), 25.8 min (major, R).

Resulting product obtained in Example 5

$^1$H NMR (400 MHz, CDCl$_3$) δ 1.41 (s, 9H), 3.65 (s, 3H), 3.74 (s, 3H), 3.83 (s, 3H), 3.86 (s, 3H), 3.88 (brs, 1H), 5.40 (brs, 1H), 6.10 (brs, 1H), 6.75-6.86 (m,3H). $^{13}$C NMR (100 MHz, CDCl$_3$) δ 28.2 (3C), 52.7, 52.9, 53.3, 55.9, 56.0, 56.8, 79.8. 109.6, 111. 1, 118.3, 132.1, 148.4, 148.9, 155.2, 167.5, 168.6. M.p. 96-97° C. IR (KBr) 3373, 2976, 1717, 1517, 1259, 1163, 1026 cm$^{-1}$. $[α]_D^{23}$=−2.4 (c 1.0, CHCl$_3$, 90% ee (R)). HRMS (FAB+) calcd for C$_{19}$H$_{27}$NNaO$_8$ [M+Na]+ 420.1634, found 420.1622. HPLC analysis; AD-H, n-hexane/i-PrOH=4/1, 1.0 mL/min, $t_R$=28.1 min (minor, S), 26.4. min (major, R).

Resulting product obtained in Example 6

$^1$H NMR (4.00 MHz, CDCl$_3$) δ 1.44 (s, 9H) 3.72 (s, 3H), 3.75 (s, 3H), 4.05 (brs, 1H), 5.54 (brs, 1H), 5.92 (brs, 1H), 6.22 (m, 1H), 6.30 (m, 1H), 7.31 (m, 1H). $^{13}$C NMR (100 MHz, CDCl$_3$) δ 28.3 (3C), 48.4, 52.7, 53.0, 54.1, 80.1, 106.8, 110.6, 142.1, 152.2, 155.1, 167.4, 168.3. IR (neat) 2978, 1719, 1497, 1367, 1248, 1165 cm$^{-1}$. $[α]_D^{24}$=−3.6 (c 1.00, CHCl$_3$, 90% ee (R)) HRMS (FAB+) calcd for C$_{15}$H$_{21}$NNaO$_7$ [M+Na]+ 350.1216, found 350.1209. HPLC analysis.; AD-H, n-hexane/i-PrOH=9/1, 1.0 mL/min, $t_R$=14.0 min (minor, S), 23.8 min (major, R).

Resulting product obtained in Example 7

$^1$H NMR (400 MHz, CDCl$_3$) δ 1.43 (s, 9H), 3.68 (s, 3H), 3.75 (s, 3H), 3.96 (brs, 1H), 5.55 (brs, 1H), 6.07 (brs, 1H), 7.00 (dd, J=5.1, 1.2 Hz, 1H), 7.14 (dd, J=3.0, 1.2 Hz, 1H), 7.28 (dd, J=5.1, 3.0 Hz, 1H). $^{13}$C NMR (100 MHz, CDCl$_3$) δ 28.3 (3C), 50.0, 52.6, 52.9, 56.1, 79.8, 121.5, 126.0, 126.4, 140.7, 155.1, 167.5, 168.5. IR (neat) 3423, 2977, 1736, 1498, 1366, 1245, 1165, 1046 cm$^{-1}$. $[α]_D^{24}$=−3.6 (c 1.00, CHCl$_3$, 95% ee (R)). HRMS (FAB+) calcd for C$_{15}$H$_{21}$NNaO$_6$S [+Na]+ 366.0987, found 366.0979. HPLC analysis; AD-H, n-hexane/i-PrOH=9/1, 1.0 mL/min, $t_R$=29.5 min (minor, S), 33.9 min (major, R).

Resulting product obtained in Example 8

$^1$H NMR (400 MHz, CDCl$_3$) δ 1.43 (s, 9H), 3.67 (s, 3H), 3.77 (s, 3H), 3.95 (brs, 1H), 5.53 (brs, 1H), 6.23 (brs, 1H), 7.28 (dd, J=7.8, 4.8 Hz, 1), 7.68 (dd, J=7.8, 1.8 Hz, 1H), 8.53 (dd, J=4.8, 1.8 Hz, 1H), 8.59 (s, 1H). $^{13}$C NMR (100 MHz, CDCl$_3$) δ 28.3 (3C), 51.6, 52.8, 53.1, 56.2, 80.3, 123.4, 134.2, 135.1, 148.2, 149.1, 155.1, 167.2, 168.1. IR (neat) 3368, 2978, 1740, 1507, 1434, 1273, 1165, 1025 cm$^{-1}$. $[α]_D^{24}$=−8.8 (c 1.00, CHCl$_3$, 89% ee (R)). HRMS (FAB+) calcd for C$_{16}$H$_{22}$N$_2$NaO$_6$ [M+Na]+ 361.1376, found 361.1381. HPLC analysis; AD-H, n-hexane/i-PrOH=4/1, 1.0 mL/min, $t_R$=18.7 min (minor,), 25.0 min (major, S).

Resulting product obtained in Example 9

$^1$H NMR (400 MHz, CDCl$_3$) δ 1.42 (s, 9H), 3.55 (s, 3H), 3.82 (s, 3H), 4.09 (brs, 1H), 6.30 (brs, 1H), 6.60 (brs, 1H), 7.42 (t, J=7.8 Hz, 1H), 7.50 (m, 2H), 7.58 (t, J=6.9 Hz, 1H), 7.77 (d, J=7.8 Hz, 1H), 7.87 (d, J=7.8 Hz, 1H), 8.11 (d, J=8.7 Hz, 1H). $^{13}$C NMR (100 MHz, CDCl$_3$) δ 28.4 (36), 50.2, 52.5, 53.2, 55.4, 79.9, 122.2, 123.7, 125.2, 125.9, 126.9, 128.6, 129.2, 130.1, 133.9, 134.8, 155.2, 167.9, 168.7. IR (neat) 3421, 2977, 1717, 1496, 1366, 1245, 1163, 1055 cm$^{-1}$. $[α]_D^{23}$=−34.4 (c 1.00, CHCl$_3$, 88% ee (R)). HRMS (FAB+) calcd for C$_{21}$H$_{25}$NNaO$_6$ [M+Na]+ 410.1580, found 410.1584. HPLC analysis; AD-H, n-hexane/i-PrOH =9/1, 1.0 mL/min, $t_R$=14.5 min (major, R), 17.1 min (minor, S).

Examples 10 to 14

Asymmetric Mannich reactions between tert-butylbenzylidene carbamate and various malonic acid diesters shown in Table 2 were carried out as in Example 1. The results thereof are shown in Table 2. In all of Examples 10 to 14, products were obtained in very high yields and with very high enantiomeric excesses. Note that the numerical values in brackets under the columns of yield and enantiomeric excess in Example 14 represent the results in the case where 2.5 mole percent of (R)-BINOL and 3.75 mole percent of n-Bu$_2$Mg were used.

TABLE 2

| | | Product | |
|---|---|---|---|
| | R | X | Yield (%) | ee (%) |
| Example 10 | n-Pr | H | 99 | 92 |
| Example 11 | Bn | H | 99 | 91 |
| Example 12 | Allyl | H | 98 | 88 |
| Example 13 | Me | Cl | >99 | 97 |
| Example 14 | Me | Br | 92, [87] | 96, [94] |

The spectrum data of the products obtained in Examples 10 to 14 are shown below.

$^1$H NMR (400 MHz, CDCl$_3$) δ 0.79 (t, J=7.2 Hz, 3H), 0.92 (t, J=7.2 Hz, 3H), 1.40 (s, 9H), 1.52 (m, 2H), 1.66 (m, 2H), 3.91 (brs, 1H), 3.99 (m, 2H), 4.10 (m, 2H), 5.49 (brs, 1H), 6.21 (brs, 1H), 7.20-7.34 (m, 5H). $^{13}$C NMR (100 MHz, CDCl$_3$) δ 10.2, 10.3, 21.7, 21.9, 2.8.3 (3C), 53.5, 57.0, 67.2, 67.6, 79.7, 126.3 (2C), 127.6, 128.6 (2C), 139.7, 155.1, 167.3, 168.3. IR. (neat) 3430, 2971, 1724, 1497, 1355, 1249, 1167, 1057 cm$^{-1}$. $[\alpha]_D^{24}$=−8.8 (c 1.0, CHCl$_3$, 92% ee (R)). HRMS (FAB+) calcd for C$_{21}$H$_{31}$NNaO$_6$ [M+Na]$^+$ 416.2049, found 416.2062. HPLC analysis.; AD-H, n-hexane/i-PrOH=9/1, 1.0 mL/min, $t_R$=14.3 min (minor, S), 19.2 min (major, R).

Resulting product obtained in Example 10.

$^1$H NMR (400 MHz, CDCl$_3$) δ 0.79 (t, J=7.2 Hz, 3H), 0.92 (t, J=7.2 Hz, 3H), 1.40 (s, 9H), 1.52 (m, 2H), 1.66 (m, 2H), 3.91 (brs, 1H), 3.99 (m, 2H), 4.10 (m, 2H), 5.49 (brs, 1H), 6.21 (brs, 1H), 7.20-7.34 (m, 5H). $^{13}$C NMR (100 MHz, CDCl$_3$) δ 10.2, 10.3, 21.7, 21.9, 28.3 (3C), 53.5, 57.0, 67.2, 67.6, 79.7, 126.3 (2C), 127.6, 128.6 (2C), 139.7, 155.1, 167.3, 168.3. IR. (neat) 3430, 2971, 1724, 1497, 1365, 1249, 1167, 1057 cm$^{-1}$. $[\alpha]_D^{24}$=−8.8 (c 1.0, CHCl$_3$, 92% ee (R)). HRMS (FAB+) calcd for C$_{21}$H$_{31}$NNaO$_6$ [M+Na]$^+$ 416.2049, found 416.2062. HPLC analysis; AD-H, n-hexane/i-PrOH=9/1, 1.0 ML/min, $t_R$=14.3 min (minor, S), 19.2 min (major, R).

Resulting product obtained in Example 11

$^1$H NMR (400 MHz, CDCl$_3$) δ 1.41 (s, 9H), 4.01 (brs, 1H), 5.04 (s, 2H), 5.12 (d, J=12.0 Hz, 1H), 5.17 (d, J=12.0 Hz, 1H), 5.56. (brs, 1H), 6.20 (brs, 1H), 7.06-7.12 (m, 2H), 7.20-7.36 (m, 13H). $^{13}$C NMR (100 MHz, CDCl$_3$) δ 28.4 (3C), 53.4, 56.8, 67.3, 67.6, 79.7, 126.2 (2C), 127.6, 128.0, 128.2 (20), 128.3, 128.4, 128.5 (2C), 128.6 (4C), 134.8, 134.9, 139.2, 139.3, 155.0, 166.8, 167.8. M.p. 105-106° C. IR (KBr) 3429, 2977, 1720, 1496, 1366, 1251, 1163, 1026 cm$^{-1}$. $[\alpha]_D^{22}$=−15.2 (c 1.00, CHCl$_3$, 91% ee (R)) HRMS (FAB+) calcd for C$_{29}$H$_{31}$NNaO$_6$ [M+Na]$^+$ 512.2049, found 512.2055. HPLC analysis;AS-E, n-hexane/i-PrOH=39/1, 1.0 mL/min, $t_R$=28.1 min (major, R), 36.6 min (minor, S).

Resulting product obtained in Example 12

$^1$H NMR (400 MHz, CDCl$_3$) δ 1.41 (s, 9H) , 3.97 (s, 1H), 4.53 (m, 2H), 4.64 (m, 2H), 5.15 (d, J=16.2 Hz, 1H), 5.16 (d, J=10.8 Hz, 1H), 5.24 (d, J=10.8 Hz,1H), 5.32 (d, J=16.2 Hz, 1H), 5.53 (brs, 1H), 5.74 (m, 1H), 5.88 (m, 1H), 6.20 (brs, 1H), 7.21-7.36. (m, 5H). $^{13}$C NMR (100 MHz, CDCl$_3$) δ 28.4 (30), 53.5, 57.0, 66.2, 66.6, 79.8, 118.8, 119.1, 126.3 (2C), 127.6, 128.7 (2C), 131.2, 131.3, 139.4, 155.1, 166.8, 167.7. IR (neat) 3429, 2975, 1720, 1496, 1367, 1249, 1165 cm$^{-1}$. $[\alpha]_D^{25}$=−8.0 (c 0.5, CHCl$_3$, 88% ee (R)) HRMS (FAB+) calcd for C$_{21}$H$_{27}$NNaO$_6$ [M+Na]$^+$ 412.1736, found 412.1737. HPLC analysis; AD-H, n-hexane/i-PrOH=9/1, 1.0 mL/min, $t_R$=23.3. min (minor, S), 33.3 min (major, R).

Resulting product obtained in Example 13

$^1$H NMR (400 MHz, CDCl$_3$) δ 1.41 (s, 9H), 3.77 (s, 3H), 3.80 (s, 3H), 5.68 (d, J=9.9 Hz, 1H), 5.97 (d, J=9.9 Hz, 1H), 7.28-7.44 (m, 5H). $^{13}$C NMR (100 MHz, CDCl$_3$) δ 28.3 (3C), 54.0, 54.1, 58.8, 73.4, 80.2, 128.2 (2C), 128.6, 128.8 (2C), 136.0, 154.3, 165.9, 166.1. IR (neat) 3439, 2978, 1719, 1494, 1367, 1255, 1166, 1022 cm$^{-1}$. $[\alpha]_D^{23}$=+3.2 (c 1.0, CHCl$_3$, 97% ee (S)). HRMS (FAB+) calcd for C$_{17}$H$_{22}$ClNNaO$_6$ [M+Na]$^+$ 394.1033, found 394.1042. HPLC analysis;AD-H× 2, n-hexane/i-PrOH=19/1, 0.5 mL/min, $t_R$=52.4 min (minor, R), 55.9 min (major, S).

Resulting product obtained in Example 14

$^1$H NMR (400 MHz, CDCl$_3$) δ 1.41 (s, 9H), 3.77 (s, 3H), 3.79 (s, 3H), 5.62 (d, J=9.9 Hz, 1H), 6.16 (d, J=9.9 Hz, 1H), 7.28-7.42 (m, 5H). $^{13}$C NMR (100 MHz, CDCl$_3$) δ 28.3 (3C), 54.0, 54.2, 59.3, 64.4, 80.2, 128.2 (2C), 128.5, 128.9 (2C), 136.4, 154.4, 166.4, 166.7. IR (neat) 3439, 2978, 1715, 1317, 1245, 1165, 1037 cm$^{-1}$. $[\alpha]_D^{24}$=+24.8 (c 0.50, CHCl$_3$, 96% ee (S)). HRMS (FAB+) calcd for C$_{17}$H$_{22}$BrNNaO$_6$ [M+Na]$^+$ 438.0528, found 438.0528. HPLC analysis AD-H×2, n-hexane/i-PrOH=19/1, 0.5 mL/min, $t_R$=45.1 min (minor, R), 54.7 min (major, S).

Example 15

In Example 15, as shown in the formula below, an asymmetric Mannich reaction between an aldimine derived from glyoxal and having a 4-methoxyphenyl group on the nitrogen atom and dimethyl malonate having a bromine atom in the α-position was carried out as in Example 1. In this case, relatively good results were obtained as shown in the formula below.

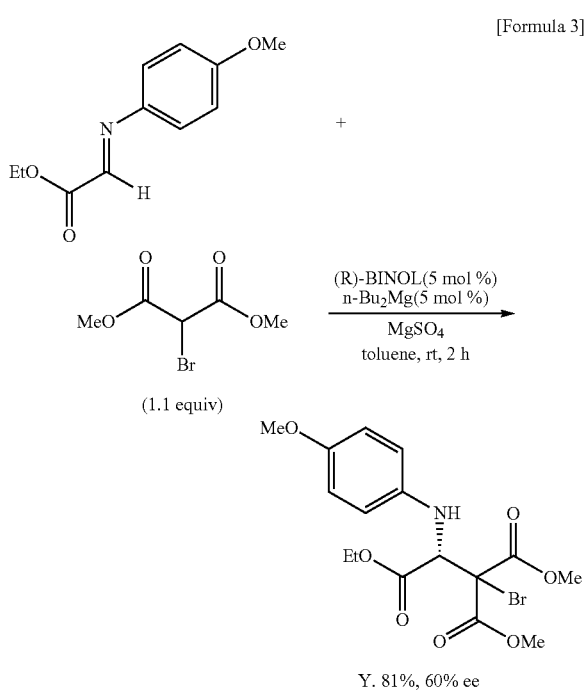

[Formula 3]

Examples 16 and 17 and Comparative Examples 1 to 6

Asymmetric Mannich reactions between tert-butylbenzylidene carbamate and dimethyl malonate were carried out in the presence of (R)-BINOL and MX shown in Table 3, under the reaction conditions shown in Table. 3, according to the procedure of Example 1. The results thereof are shown in Table 3. As is obvious from Table 3, in all of Comparative Example 1 in which (R)-BINOL only was used, Comparative Examples 2 and 4 in which (R)-BINOL and n-BuLi were used, and Comparative Examples 3 and 5 in which (R)-BINOL, n-BuLi, and t-BuOH were used, the enantiomeric excesses were low although the reactions proceeded in some cases. Furthermore, in Comparative Example 6 in which 5 mole percent of (R)-BINOL and 2.5 mole percent of n-Bu$_2$Mg were used (BINOL/Mg molar ratio=1/0.5), the reaction hardly proceeded. In contrast, in Example. 16 in which 5 mole percent of (R)-BINOL and 5 mole percent of n-Bu$_2$Mg were used (BINOL/Mg molar ratio=1/1), both the yield and the enantiomeric excess were very high. Furthermore, in Example 17 in which 5 mole percent of (R)-BINOL and 10 mole percent of n-Bu$_2$Mg were used (BINOL/Mg molar ratio=1/2), the yield was equivalent to that of Example 16, and the enantiomeric excess was sufficiently high although it was slightly lower than that of Example 16.

TABLE 3

Boc-N=CH-Ph + MeO-C(O)-CH₂-C(O)-OMe (1.1 equiv) → [(R)-BINOL (5 mol %), MX (0-10 mol %), MgSO₄, toluene] → Boc-NH-CH(Ph)-CH(C(O)OMe)₂

| MX: Numerical value in bracket( ) represent mol % | Reaction condition | Product Yield (%) | ee (%) |
|---|---|---|---|
| Comparative Example 1 | — | rt, 24 h | 0 | — |
| Comparative Example 2 | n-BuLi(5) | −40° C., 6 h | <3 | — |
| Comparative Example 3 | n-BuLi(5) + t-BuOH(10) | −40° C., 6 h | 98 | 0 |
| Comparative Example 4 | n-BuLi(10) | −40° C., 6 h | >99 | 28 |
| Comparative Example 5 | n-BuLi(10) + t-BuOH(20) | −40° C., 6 h | 99 | 0 |
| Comparative Example 6 | n-Bu₂Mg(2.5) | −40° C., 6 h | 14 | — |
| Example 16 | n-Bu₂Mg(5) | −40° C., 6 h | 98 | 92 |
| Example 17 | n-Bu₂Mg(10) | −40° C., 6 h | 97 | 80 |

Comparative Example 7

In Comparative Example 7, an reaction was carried out as in Example I except that (R)-BINOL having 3,4,5-trifluorophenyl groups introduced in the 3,3' positions and n-Bu₂Mg each in an amount of 2.5 mole percent were used and the reaction time was set to be 2 hours. As a result, the corresponding β-aminocarbonyl compound was hardly obtained. Furthermore, when n-Bu₂Mg was doubled to 5 mole percent and the reaction time was set to be 5 hours, the corresponding β-aminocarbonyl compound was obtained in a yield of 88%, but the enantiomeric excess was only 35% ee. This shows that in order to obtain a target product with a high enantiomeric excess, substituents in the 3,3' positions of (R)-BINOL are not required.

The present application claims priority from Japanese Patent Application No. 2010-150995 filed on Jul. 1, 2010, the entire contents of which are incorporated in the present specification by reference.

Industrial Applicability

The present invention is applicable in the pharmaceutical/chemical industry, and can be used in the production of various -aminocarbonyl compounds, which are used, for example, as intermediates for medical drugs, agricultural chemicals, and cosmetics.

The invention claimed is:

1. A method for producing a β-aminocarbonyl compound comprising carrying out a Mannich reaction between an aldimine in which nitrogen is protected and a malonic acid diester, in the presence of optically active BINOL and dialkyl magnesium in which two alkyl groups are the same or different in an amount 1 to 2 molar times the amount of the BINOL, to obtain an optically active β-aminocarbonl compound.

2. The method for producing a β-aminocarbonyl compound according to claim 1, wherein the aldimine is a compound represented by $R^1$—CH=$NR^2$ wherein $R^1$ is an aryl group or an ester group, and $R^2$ is tert-butoxycarbonyl (Boc), benzyloxycarbonyl (Cbz), 2,2,2-trichloroethoxycarbonyl (Troc), a phenyl group, a 2-methoxyphenyl group, a 4-methoxyphenyl group, or a naphthyl group.

3. The method for producing a β-aminocarbonyl compound according to claim 1, wherein the malonic acid diester is a compound represented by $CHX(CO_2R^3)_2$ wherein X is a hydrogen atom or a halogen atom, and $R^3$ is alkyl, allyl, benzyl, or aryl.

4. The method for producing a β-aminocarbonyl compound according to claim 1, wherein the BINOL is used in an amount of 2.5 mole percent to 10 mole percent relative to the aldimine.

5. The method for producing a β-aminocarbonyl compound according to claim 1, wherein an aromatic solvent or a halogenated hydrocarbon solvent is used as a reaction solvent.

* * * * *